(12) United States Patent
Wakai et al.

(10) Patent No.: US 8,343,776 B2
(45) Date of Patent: Jan. 1, 2013

(54) IMMUNOASSAY METHOD

(75) Inventors: Junko Wakai, Kyoto (JP); Akihito Kamei, Kyoto (JP); Jin Muraoka, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/222,599

(22) Filed: Aug. 31, 2011

(65) Prior Publication Data

US 2011/0312104 A1 Dec. 22, 2011

(30) Foreign Application Priority Data

Nov. 25, 2009 (JP) .................................. 2009-267109
May 27, 2010 (JP) ..................... PCT/JP2010/003573

(51) Int. Cl.
*G01N 33/543* (2006.01)

(52) U.S. Cl. ......... 436/518; 435/7.1; 435/7.92; 436/501

(58) Field of Classification Search .................... None
See application file for complete search history.

(56) References Cited

U.S. PATENT DOCUMENTS

| | | | | |
|---|---|---|---|---|
| 7,241,578 | B2 * | 7/2007 | Yugawa et al. | 435/7.1 |
| 2002/0160428 | A1 * | 10/2002 | Sundrehagen | 435/7.9 |
| 2009/0098583 | A1 | 4/2009 | McDonald et al. | |
| 2009/0156422 | A1 | 6/2009 | Punyadeera et al. | |

FOREIGN PATENT DOCUMENTS

| | | |
|---|---|---|
| EP | 0 585 914 A2 | 3/1994 |
| EP | 0 629 857 A2 | 12/1994 |
| JP | 02-073158 | 3/1990 |
| JP | 05-273212 | 10/1993 |
| JP | 06-174712 | 6/1994 |
| JP | 07-063759 | 3/1995 |
| JP | 11-153600 | 6/1999 |
| JP | 2001-013144 | 1/2001 |
| JP | 2007-225417 | 9/2007 |
| JP | 2009-020120 | 1/2009 |
| JP | 2009-240235 | 10/2009 |
| JP | 2009-539102 | 11/2009 |

* cited by examiner

*Primary Examiner* — Gary W Counts
(74) *Attorney, Agent, or Firm* — McDermott Will & Emery LLP

(57) ABSTRACT

Provided is an immunoassay method that can reduce the effort of establishing an immunoassay system due to not needing two or more antibodies, and that is applicable to not only high molecular weight antigens but also to low molecular weight antigens such as hapten. The method is for releasing, from a surface of a base plate, immunoglobulin G antibody bound to the surface via protein A. The method includes the following steps (A) and (B): (A) a step of preparing the base plate having the surface to which immunoglobulin G antibody produced by a producer cell line of deposit No. FERM BP-10459 is bound via protein A; and (B) a step of providing a solution (from pH 6 to pH 8.9; preferably, from pH 7.4 to pH 8.9) containing human serum albumin onto the surface so as to release the immunoglobulin G antibody from the protein A.

21 Claims, 11 Drawing Sheets

IMMUNOASSAY METHOD

RELATED APPLICATIONS

This application is a continuation of International Application No. PCT/JP2010/006831, filed on Nov. 22, 2010, which in turn claims the benefit of Japanese Application No. 2009-267109, filed on Nov. 25, 2009, and International Application No. PCT/JP2010/003573, filed May 27, 2010, the disclosures of which Applications are incorporated by reference herein.

BACKGROUND OF THE INVENTION

1. Field of the Invention

The present invention relates to a method for releasing, from a surface of a base plate, immunoglobulin G bound to the surface with use of protein A.

2. Description of the Background Art

Protein A is a protein that makes up 5% of the cell wall components of *Staphylococcus aureus*, and is abbreviated as "SpA." Protein A has a high affinity to immunoglobulin G Protein A is interposed between the surface of the base plate and immunoglobulin G so as to immobilize immunoglobulin G on the surface of the base plate. Patent Literature 1 (lines 3-4 in the lower right column of page 3) discloses that although immunoglobulin G is bound to protein A, immunoglobulin G is released from protein A by lowering the pH. By taking advantage of the releasing caused by the lowering of the pH, a target substance contained in a biological sample can be detected or quantified.

CITATION LIST

Patent Literature

[PTL 1] Japanese Laid-Open Patent Publication No. H02-073158

Problems to be Solved by the Invention

Lowering of the pH can cause undesirable denaturation of a biological sample. In addition, lowering the pH may increase the number of steps required.

Solution to the Problems

The present inventors have discovered that, when a biological sample containing human serum albumin is supplied to a surface to which immunoglobulin IgG antibody consisting of an anti-human albumin monoclonal antibody (2F13F11G11) produced by a producer cell line of deposit No. FERM BP-10459 is bound via protein A, the immunoglobulin IgG antibody is released from protein A even if the pH of the biological sample is not lower than 6, and preferably not lower than 7.4.

The present invention provides a method for releasing, from a surface of a base plate, immunoglobulin G (IgG) antibody bound to the surface via protein A. This method comprises the following steps: (A) a step of preparing the base plate having the surface to which immunoglobulin G antibody is bound via protein A; and (B) a step of providing a solution containing human serum albumin onto the surface so as to release the immunoglobulin G antibody from the protein A. Here the immunoglobulin G antibody is an anti-human albumin monoclonal antibody (2F13F11G11) produced by a producer cell line of deposit No. FERM BP-10459, and the solution has a pH of not lower than 6 and not higher than 8.9.

As used herein, the term "protein A" is a protein also referred to as "SpA." This protein has been discovered as a cell wall component of *Staphylococcus aureus*. A person skilled in the art can acquire a natural or a synthetic protein A from a commercial supply source.

In one embodiment, at the above described step (B), a complex of the immunoglobulin G antibody and the human serum albumin is formed through antigen-antibody reaction.

As used herein, the term "complex" refers to a group of molecules that results from binding of two or more molecules via interaction with one another, and that behaves as if being a single molecule. The group of molecules behaving as if being a single molecule can be formed from binding, via interaction, of multiple molecules including, for example, polypeptides, polynucleotides, lipids, sugars, and small molecules. In the above described example of the present specification, a group of molecules behaving as a single molecule is obtained from binding of the immunoglobulin G antibody and the human serum albumin molecule via interaction.

As used herein, the term "interaction" with reference to two substances (molecules), means that one substance influences the other substance via forces (e.g., intermolecular forces (Van der Waals force), hydrogen bond, hydrophobic interactions, or the like). Typically, two substances interacting with each other interact in the manner of association or binding.

As used herein, the terms "binding," means the presence of a physical or chemical interaction between two proteins or compounds or associated proteins or compounds or combinations thereof. Binding includes ionic, non-ionic, hydrogen, Van der Waals, hydrophobic interactions and the like. A physical interaction (binding) can be either direct or indirect. Indirect interactions may be through or due to the effects of another protein or compound. Direct binding refers to interactions that do not take place through, or due to, the effect of another protein or compound, but instead are without other substantial chemical intermediates.

In another embodiment, the immunoglobulin G antibody may be released from the surface when the complex is formed.

It should be noted that, after the immunoglobulin G antibody has been released from the surface, the complex that existed at the time of releasing does not necessarily have to stably exist; and even if the binding in the complex is dissolved upon the releasing, a system for appropriate measurements can be established by the subsequent steps if necessary.

In another embodiment, at the above described step (B), the solution may contain the immunoglobulin G antibody which has been released from the surface.

In still another embodiment, after the above described step (B), the solution may contain the complex.

In still another embodiment, the above described pH is not lower than 7.4 and not higher than 8.9.

In still another embodiment, the solution may be a buffer solution. More preferably, the pH is not lower than 7.4 and not higher than 8.9.

In another aspect, by utilizing the above described method for releasing, from a surface of a base plate, immunoglobulin G (IgG) antibody bound to the surface via protein A, the present invention can provide a method for quantifying an analyte contained in a solution, or a method for determining whether the solution contains the analyte. Here, the immunoglobulin G antibody, which is bound to the surface of the base plate via the protein A, is modified with a suitable label. In addition, the immunoglobulin G antibody interacts with the analyte (human serum albumin) existing in the solution, and is released from the protein A. The released immunoglobulin G antibody is mixed into the solution; and detection of the presence of the analyte and quantification of the analyte are achieved by detecting the presence of the label bound to the immunoglobulin G antibody or the amount of the label in the solution.

In another aspect, by utilizing the above described method for releasing, from a surface of a base plate, immunoglobulin G antibody bound to the surface via protein A, the present invention provides a device in which an immunoassay method is executed.

The device for executing the immunoassay method according to one embodiment of the present invention includes, for example, an antibody (immunoglobulin G antibody produced by a producer cell line of deposit No. FERM BP-10459) that specifically binds to an analyte modified at least by a label, a binder (protein A) that specifically binds to the antibody, and a support (e.g., a base plate).

The immunoassay method performed in the device includes the following steps:

(1) a step of providing an analyte to the antibody immobilized on the support via the binder;
(2) a step of forming a complex of the antibody and the analyte through antigen-antibody reaction;
(3) a step of dissolving the binding between the antibody and the binder to release the support, when the complex of the antibody and the analyte is formed; and
(4) a step of measuring the amount of the label of the released antibody.

The step of measuring the amount of the label of the released antibody may be achieved by any method, as long as it is a method that quantifies the label by using a chemical property or a physical property of the label.

Advantageous Effects of the Invention

The present invention establishes an immunoassay system which includes easy steps and which only uses a single type of antibody that specifically binds to an antigen. This allows providing an immunoassay method and device capable of measuring analytes that are not only antigens with a high molecular weight but also antigens with a low molecular weight.

Many biological samples have a neutral pH. In the present invention, a biological sample can be used as a solution without performing a step of lowering the pH. Therefore, adverse influences to the biological sample due to lowering of the pH can be avoided.

DESCRIPTION OF THE PREFERRED EMBODIMENTS

In the following, an illustrative embodiment of the present invention is described with reference to the drawings.

Mouse-Mouse Hybridoma that produces cell line 2F13F11G11, Accession No. FERM BP-10459 was deposited on Nov. 30, 2005 at the National Institute of Advanced Industrial Science and Technology, located at 1-1, Higashi 1-chome Tsukuba-shi, Ibaraki-ken 305-8566 Japan, in accordance with the terms of the Budapest Treaty.

Embodiment 1

Figure 1:
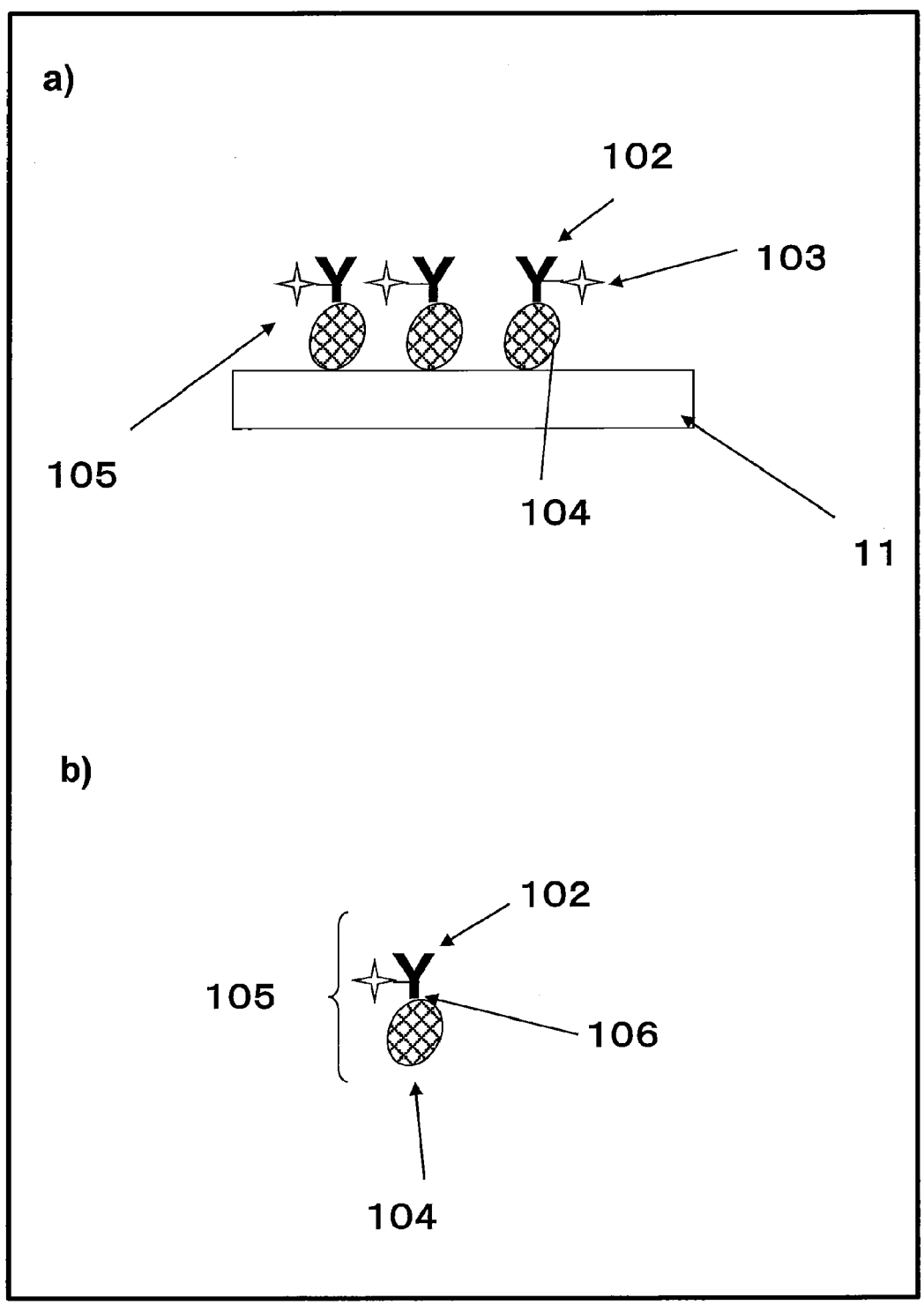
FIG. 1 is a basic configuration figure of an immunoassay method according to the present invention.

FIG. 1 is a basic configuration figure of an immunoassay method of Embodiment 1. An antibody 102 is an antibody that specifically binds to an analyte. A label 103 is a label that binds to the antibody 102. As shown in FIG. 1(a), the antibody 102 is immobilized on a support 11 via a binder 104. As shown in FIG. 1(b), the antibody 102 binds to the binder 104 to form an antibody-binder complex 105. The antibody-binder complex 105 includes the antibody 102 and the binder 104 bound to a binder binding site 106 of the antibody 102.

There is no particular limitation in the support 11, as long as the binder 104 can be immobilized thereon. Specifically, the support 11 includes, for example, a glass or resin base plate having a metal film on a surface thereof.

The antibody 102 bound to the binder 104 via the binder binding site 106 has a property of being released from the binder 104 when an analyte is bound to the antibody 102. Specific examples of the antibody 102 include IgG antibody. More specifically, the antibody 102 is an anti-human albumin monoclonal antibody (2F13F11G11) produced by a producer cell line of deposit No. FERM BP-10459. Here, the analyte (e.g., as represented as 101 in FIG. 2, which is described later) is human serum albumin (hSA). When hSA is supplied, the antibody 102, i.e., the anti-human albumin monoclonal antibody, can interact with and bind to the hSA.

The binder 104 binding to the antibody 102 has a property of releasing the antibody 102 when the analyte is bound to the antibody 102. Specifically, the binder includes, for example, protein A.

The label 103 is a substance that can be used for optically or electrochemically measuring the amount of the antibody 102. Specific examples of the label 103 include, but not limited to, enzymes such as horseradish peroxidase, alkaline phosphatase, and beta-galactosidase, light-emitting dyes such as fluorescent dyes, ruthenium complexes, and luminol, and electrochemically active substances such as ferrocene, and the like.

One example of the immunoassay method of the present invention is described below.

Figure 2:
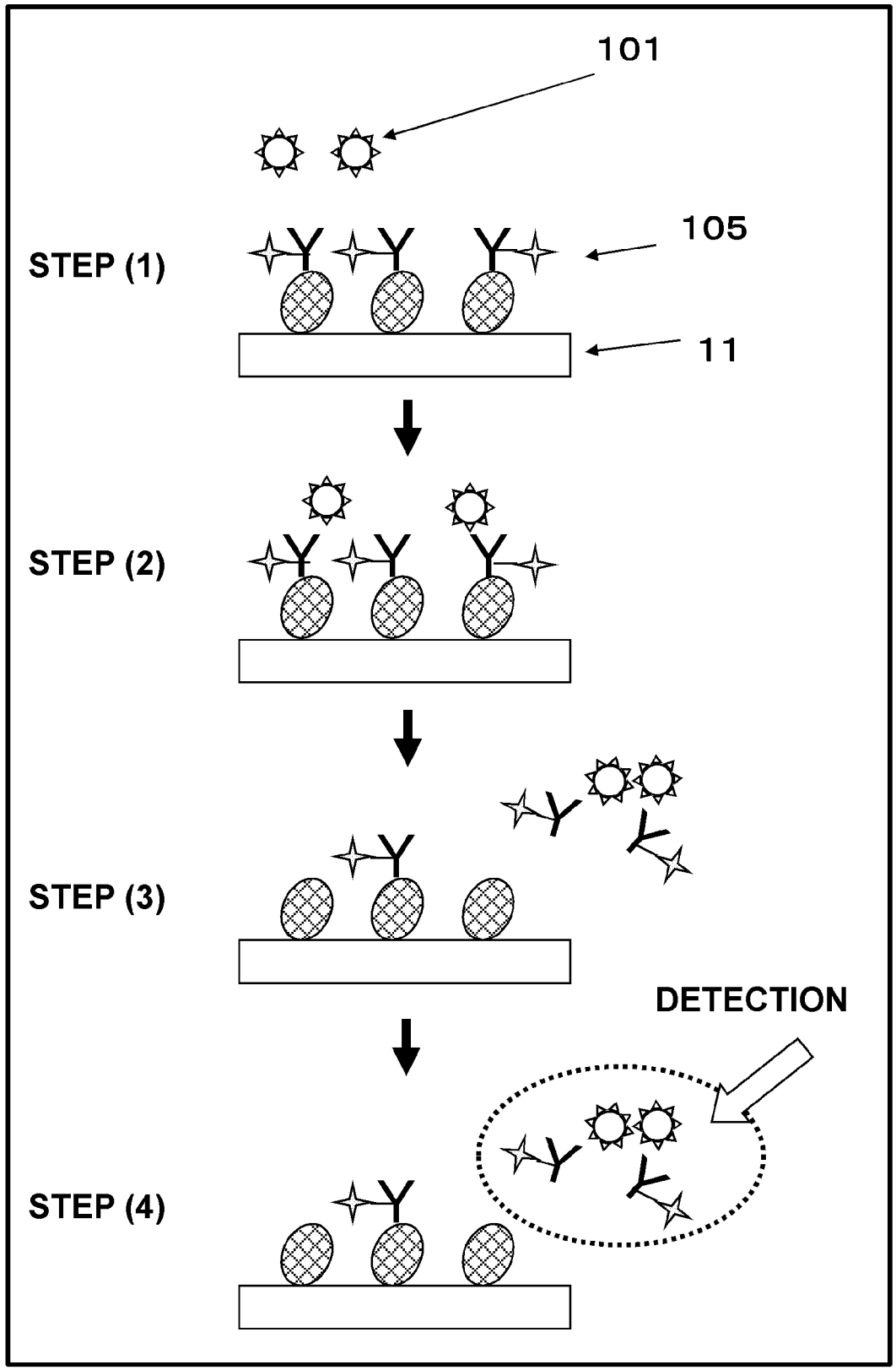
FIG. 2 shows a measurement flow of the immunoassay method according to the present invention.

FIG. 2 shows a measurement flow of the immunoassay method of Embodiment 1. This method includes the following steps (1) to (4).

In step (1), a solution containing an analyte 101 is supplied to the support 11 having the antibody-binder complex 105.

The pH of the solution is not lower than 6 and not higher than 8.9. The pH is preferably not lower than 7.4 and not higher than 8.9.

In step (2), a complex of the analyte 101 and the antibody 102 is formed through an antigen-antibody reaction.

In step (3), when the complex of the analyte 101 and the antibody 102 is formed, the antibody 102 is released from the binder 104. As described above, the analyte 101 is human serum albumin (hSA). Although it is apparent from an illustrative example described later, when bovine serum albumin (BSA) is used instead of the hSA, the antibody 102 (immunoglobulin antibody IgG) is not released from the binder 104.

In step (4), the amount of the label 103 bound to the released antibody 102 is measured to calculate the amount of the released antibody 102. In this manner, the analyte 101 contained in the solution is quantified. Alternatively, in step (4), the label 103 bound to the released antibody 102 is detected to determine whether or not the solution contains the analyte 101.

A simple immunoassay is enabled based on the principle that when a sample containing an antigen is reacted with an antibody-binder complex and when the antigen is bound to the antibody, the antibody becomes released from the binder. In addition, since the method for detecting the label 103 can be selected in accordance with the property of the label used, the immunoassay method of Embodiment 1 is easily applied to a conventional immunoassay method.

Example of an Immunochromatographical Measurement Kit

Figure 3:
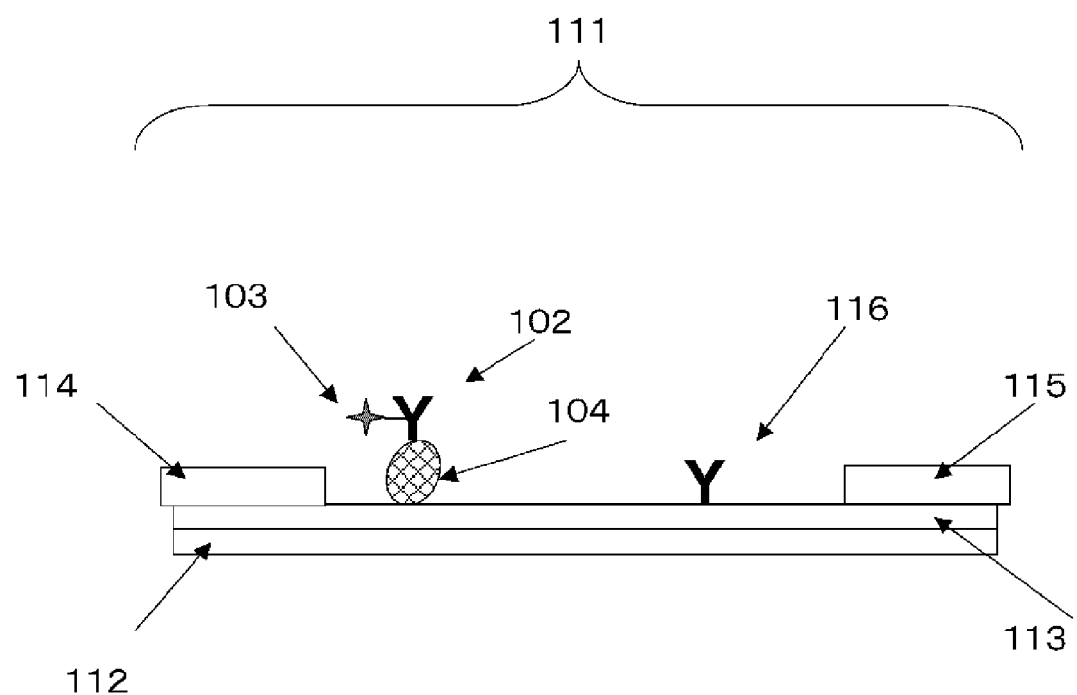
FIG. 3 shows an application of the immunoassay method according to the present invention to immunochromatography.

Described below is an example of utilizing the above described immunoassay method to an immunochromatographical measurement kit including an immunochromatographical test piece and a test solution. FIG. 3 shows the example in which the immunoassay method of Embodiment 1 is applied to the immunochromatographical measurement kit. The immunochromatographical measurement kit involves passing a substance ("mobile phase") including a sample through the surface or interior portion of a specific substance ("stationary phase or support") to have an antigen (an analyte) in the sample subjected to interaction with a labeled antibody. This allows the determination of whether or not the analyte exists.

The immunochromatographical test piece provides the stationary phase and an accompanying structural body. The immunochromatographical test piece is produced from a material having characteristics (for example, with respect to the structure or physical property of the material) that result in capillary action. Preferably, the immunochromatographical test piece is a nitrocellulose membrane which is a porous support. Proteins can be easily immobilized on the nitrocellulose membrane. However, nitrocellulose membranes are fragile. Therefore, the nitrocellulose membrane is used as being affixed to a polytetrafluoroethylene base plate (hereinafter, referred to as a PTFE base plate). Furthermore, a nitrocellulose membrane supported by a PTFE base plate is commercially available.

In an example in FIG. 3, a porous support made of a nitrocellulose membrane 113 (e.g., width 1 cm×length 6 cm, thickness 200 μm) is affixed to a PTFE base plate 112 (e.g., width 1 cm×length 10 cm, thickness 3 mm) by using a spray adhesive. At one end of the nitrocellulose membrane 113 in the length direction thereof, the nitrocellulose membrane 113 includes a sample solution introduction portion 114 made of a glass fiber filter paper. At the other end of the nitrocellulose membrane 113 in the length direction thereof, the nitrocellulose membrane 113 includes a liquid absorption portion 115 made of a liquid absorptive pad made of glass fiber.

An immunochromatographical test piece 111 does not necessarily have to include the liquid absorption portion. The immunochromatographical test piece has a certain length that prevents it from becoming completely saturated by a sample solution introduced as a mobile phase.

In the present example, the immunochromatographical test piece 111 includes, sequentially in the length direction of the nitrocellulose membrane 113 along a pathway through which the mobile phase moves, a label immobilization portion and a determination portion.

In the present example, the antibody 102 labeled by the label 103 is immobilized on the nitrocellulose membrane 113 via the binder 104 to form the label immobilization portion.

The antibody 102 is an IgG antibody capable of specifically binding to the analyte 101. When the analyte 101 is human serum albumin, the antibody 102 is preferably an IgG antibody produced by a producer cell line of deposit No. FERM BP-10459 (i.e., anti-human albumin monoclonal antibody (2F13F11G11)).

The label 103 may be, for example, enzymes such as horseradish peroxidase and alkaline phosphatase. Various methods for binding such enzymes to the antibody 102 are established.

For example, a glutaraldehyde method, a periodic acid method, and a maleimide method are known as the labeling method for horseradish peroxidase.

Commercially available labeling kits can be used such as the commonly used Peroxidase Labeling Kit-$NH_2$ which can label a $NH_2$ group in an antibody, and Peroxidase Labeling Kit-SH which can label a SH group in an antibody (both manufactured by Dojindo Laboratories).

The commercially available kits can easily label an antibody with an enzyme.

Preferably, the binder 104 is protein A.

A second antibody 116 is immobilized on the nitrocellulose membrane 113 to form the determination portion described above.

An anti-human IgG antibody obtained by immunizing an animal with the Fc region of or the whole of the IgG antibody (2F13F11G11) molecule can be used as the second antibody 116. Preferably, the second antibody 116 is an antibody obtained by immunizing an animal with the Fc region of the human IgG antibody. The antibody thus obtained does not interfere with the binding between the antibody 102 and the analyte.

The binder 104 and the second antibody 116 are immobilized on the nitrocellulose membrane 113 as described below.

A 100 μl PBS buffer solution (8 g/l NaCl, 0.2 g/l KCl, 1.15 g/l $Na_2HPO_4.12H_2O$, 0.2 g/l $KH_2PO_4$, pH 7.4) in which 1 mg/ml of protein A (the binder 104) is dissolved, is applied to a location 2 cm away from one end of the nitrocellulose membrane 113 in the length direction thereof by using a dispenser.

A 100 μl PBS buffer solution in which the second antibody 116 is dissolved (concentration: 1 mg/ml) is applied to a location 2 cm away from the other end of the nitrocellulose membrane 113 in the length direction thereof by using the dispenser.

Then, the base plate 112 is dried for two hours at 40° C.

After immobilizing the binder 104 and the second antibody 116 on the nitrocellulose membrane 113, preferably, a blocking process is performed on the nitrocellulose membrane 113 with a substance that does not participate in an antigen-antibody reaction. As a result of the blocking process, the antibody 102 is prevented from nonspecifically binding to the nitrocellulose membrane 113 without the binder 104. In addition, components contained in the sample are prevented from binding to the nitrocellulose membrane 113 during the measurement. The blocking process is performed, for example, as described below: the nitrocellulose membrane 113 is immersed in a PBS buffer solution containing 1 wt % casein for around 15 minutes to bind the casein to the nitrocellulose membrane 113.

After the blocking process, the nitrocellulose membrane 113 is washed by shaking for around 15 minutes in a container holding a PBS buffer solution to remove excessive casein. The washed nitrocellulose membrane 113 is dried once again for around two hours at 40° C. Then, a 100 µl PBS buffer solution in which the antibody 102 having the label 103 is dissolved at a concentration of 1 mg/ml is applied to the label immobilization portion using the dispenser. Then, the nitrocellulose membrane 113 is kept still at room temperature for around one hour to bind the antibody 102 having the label 103 to the binder 104.

After being kept still, the nitrocellulose membrane 113 is washed through shaking for around 15 minutes in a container holding a PBS buffer solution. As a result, the excess antibody 102 which has been deposited but did not bind to the binder 104 is removed. After the washing, the nitrocellulose membrane 113 is dried for around two hours at 40° C. Accordingly, the label immobilization portion and the determination portion can be formed on the nitrocellulose membrane 113.

Producing the immunochromatographical test piece 111 is accomplished by the procedures described above.

The test solution is a reaction solution used for identifying the amount of the label 103. The test solution can be prepared as described below.

When enzymes such as horseradish peroxidase and alkaline phosphatase are used as the label 103, the test solution is composed of liquid A and liquid B as describe next. The liquid A provides a substrate necessary for an enzyme reaction, while the liquid B provides $H_2O_2$ necessary for the enzyme reaction.

An HBS buffer solution (0.05 M HEPES-Na, 0.15 M NaCl, pH 7.5) in which, for example, 3,3'-diaminobenzidine is dissolved as a substrate at a concentration of 0.5 mg/ml is prepared (liquid A). Preferably, the liquid A is shielded from light when being stored.

In order to supply $H_2O_2$ required for the enzyme reaction, an HBS buffer solution containing 0.15% $H_2O_2$ is prepared (liquid B). The liquids A and B are mixed upon usage to obtain the test solution.

The following describes a method for using the immunochromatographical measurement kit including the obtained immunochromatographical test piece and test solution.

A sample solution is dropped on the sample solution introduction portion 114 made of a glass fiber filter paper. Then, the sample solution moves through the nitrocellulose membrane 113 via capillary action to reach the label immobilization portion composed of a complex of the binder 104 and the antibody 102.

When an analyte exists in the sample solution, the analyte becomes bound to the antibody 102 modified with the label 103. Then, a complex of the analyte and the antibody 102 is formed, and this formed complex becomes released from the binder 104 immobilized on the nitrocellulose membrane 113. The flow of the sample solution moving through the nitrocellulose membrane 113 by capillary action carries the complex to the determination portion. When the complex reaches the determination portion, the complex becomes bound to the second antibody 116. Even if the analyte and the antibody 102, which form the complex, become separated from each other while moving through the nitrocellulose membrane 113, the antibody 102 can bind to the second antibody 116. Since the antibody 102 is modified with the label 103, similarly to the formed complex, the antibody 102 can be a determination target at the determination portion.

Excess sample solution and molecules that was not bound to the determination portion move further through the nitrocellulose membrane 113 by capillary action, and are absorbed at the liquid absorption portion 115.

After the sample solution is verified to have reached the liquid absorption portion 115 and the sample solution dropped into the sample solution introduction portion is verified to be gone, the solution (the mixture containing the liquids A and B described above) containing $H_2O_2$ and the substrate-dissolved solution is dropped. A position of dropping is between the determination portion and the label immobilization portion and the dropping is conducted from the upstream side close to the determination portion. After a certain period of time has elapsed since the dropping of the mixture of the liquids A and B, coloring of the determination portion is determined visually or by using an instrument.

Similar to the application to immunochromatography, the applications of the immunoassay method of Embodiment 1 to chemical luminescence and electrochemical luminescence are conducted easily.

EXAMPLE 1

A specific example of the immunoassay method of the present invention is shown below. In the present example, measurements were performed by using a Surface Plasmon Resonance device (hereinafter, referred to as a SPR device). Specifically, BIACORE 3000 system (manufactured by Biacore AB; hereinafter, referred to as Biacore) was used as a measuring device. This measuring device is an analysis device taking advantage of surface plasmon resonance phenomena as the measurement principle, allowing detection of interactions between biomolecules without using a label. In order to measure the interactions between measuring target molecules by using the BIACORE, one of the measuring target molecules is immobilized on a measuring chip, and a sample solution containing a molecule that acts on the immobilized molecule is fed onto the surface of the measuring chip. The measuring device detects, as a surface plasmon resonance signal, a minute amount of mass changes resulting from binding and releasing of molecules occurring on the surface of the measuring chip; and the signal is chronologically monitored and the monitored result is stored as a sensorgram.

In the present example, CM 5 (manufactured by Biacore AB; hereinafter, referred to as a sensor chip) was used as the measuring chip. This sensor chip comprises carboxymethyl dextran on a gold film surface of a glass plate. When a sample is immobilized on the sensor chip, carboxyl groups of carboxymethyl dextran are activated with a proper reagent (e.g., N-hydroxy succinimide (NHS)), and then the to-be-immobilized sample is introduced thereto. The coupling (amino coupling) between the carboxyl groups included in the dextran and amino groups included in the sample allows the binder to be immobilized on the sensor chip.

The analyte, antibody, and binder used for the evaluation are shown below. Human albumin (hereinafter, referred to as hSA) was used as the analyte. Human albumin manufactured by Sigma Co., Ltd., was used as the human albumin. The antibody used in the present measurement example was an anti-human albumin monoclonal antibody produce by a producer cell line of deposit No. FERM BP-10459 (hereinafter, referred to as 2F13F11G11). Protein A (Lot# D33524) manufactured by Calbiochem Co., Ltd., was used as the binder.

Next, described below is a measuring protocol in which a change in the amount of the binding between the antibody and the binder, under conditions of presence or absence of an antigen (i.e., the analyte) was measured.

First, the binder (protein A) was immobilized on the sensor chip through amino coupling as described above. The immobilizing was performed in accordance with a immobilizing method provided by BIACORE. Protein A diluted in an acetic acid buffer solution that had a predetermined pH was used when the immobilizing is performed. It was necessary to determine the pH of the acetic acid solution in order to immobilize a sufficient amount of protein A. Prepared were solutions in which protein A at a concentration of 20 ng/ml was dissolved in 10 mM acetic acid buffer solutions each having a pH of 4, 5, and 6. Each of the prepared solutions having different pH was sequentially passed through either one of the four flow cells included in the BIACORE at a flow rate of 10 gl/min. The pH for immobilizing a sufficient amount of protein A was determined based on the sensorgrams obtained for each of the prepared solutions.

In the present experiment, a condition of pH 4 that yielded the highest amount of immobilization onto the sensor chip was adopted. At this condition of pH 4, protein A was immobilized onto the sensor chip at around 5 $ng/mm^2$. Furthermore, in order to measure a blank value, a sensorgram was obtained at a condition in which protein A did not become immobilized onto the flow cell.

Next, the BIACORE was used to measure the change in the amount of binding between the antibody and protein A under conditions of presence or absence of the antigen.

First, buffer solutions having 2F13F11G11 dissolved therein were passed through all the four flow cells at a flow rate of 20 µl/min for a flow volume of 10 µl to bind to the protein A immobilized on the sensor chip. Here, the concentration of the 2F13F11G11 dissolved in the buffer solution was 200 nM. Furthermore, the amount of binding to protein A was around 5 $ng/mm^2$. After 2F13F11G11 was passed through the flow cells, the buffer solution alone was passed through the flow cells in order to remove any influences of substances other than the 2F13F11G11 bound to protein A. In the present experiment, a PBS buffer solution (pH 7.4) containing 0.05% TWEEN 20 was used as a buffer solution.

Figure 4:
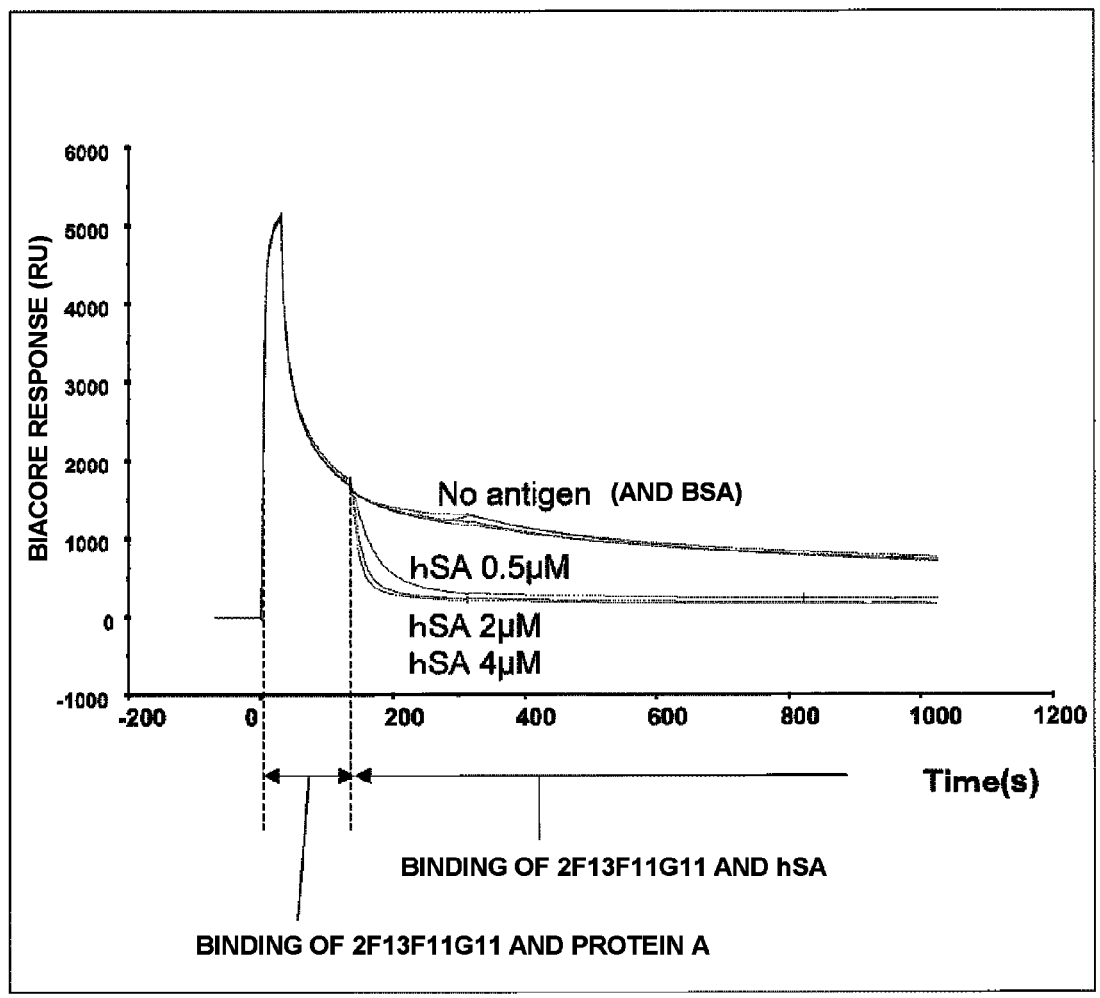
FIG. 4 is a sensor graph measured in Example 1.

Next, a buffer solution having hSA dissolved therein, which was the analyte, was passed through the flow cells to allow reaction with 2F13F11G11. Here, the flow rate was 20 µl/min, and the flow volume was 60 µl. The used concentrations of hSA were 4 µM, 2 µM, 500 nM, and 0 nM. FIG. 4 shows the sensorgram obtained as a result of the measurements. FIG. 4 also shows the result of the following Comparative Example 1.

COMPARATIVE EXAMPLE 1

In order to measure the specificity between hSA and 2F13F11G11, a similar experiment (pH: 7.4) was performed by using, instead of hSA, bovine serum albumin (hereinafter, referred to as BSA), which does not react with 2F13F11G11.

As understood from FIG. 4, a reduction in response was observed when hSA was passed through the flow cells. However, such a reduction in response was not observed immediately after BSA was passed through the flow cells. This indicates that the complex of hSA and 2F13F11G11 was released from protein A at even at a pH of 7.4 due to a specific reaction between hSA and 2F13F11G11.

It was demonstrated that the immunoassay method of the present invention is achievable through a usage of the above described antibody that specifically reacts with the analyte and that becomes released from protein A due to the reaction.

COMPARATIVE EXAMPLE 2

Experiments (pH: 7.4) were conducted similarly to those described in Example 1 by using antibody 11-4B, antibody 42-DA3, and antibody 13-3B instead of 2F13F11G11.

Antibody 11-4B was an anti-human albumin monoclonal antibody produced by a producer cell line of deposit No. FERM BP-7937.

Antibody 42-DA3 was an anti-human albumin monoclonal antibody produced by a producer cell line of deposit No. FERM ABP-10637.

Antibody 13-3B was an anti-human albumin monoclonal antibody produced by a producer cell line of deposit No. FERM BP-7938.

Figure 9:
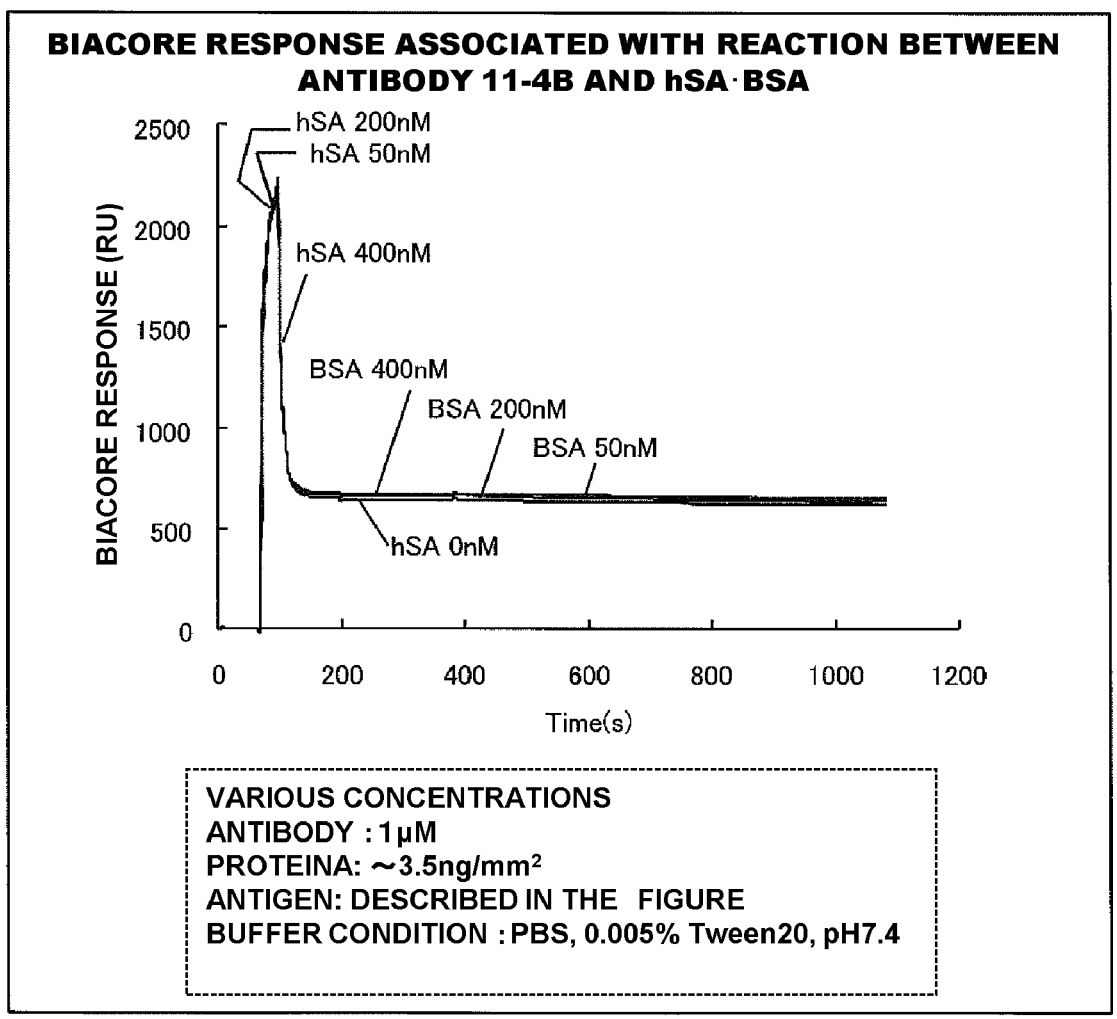
FIG. 9 is a sensor graph measured in Comparative Example 2.

FIG. 9 shows a sensorgram obtained from the measurements using antibody 11-4B.

Figure 10:
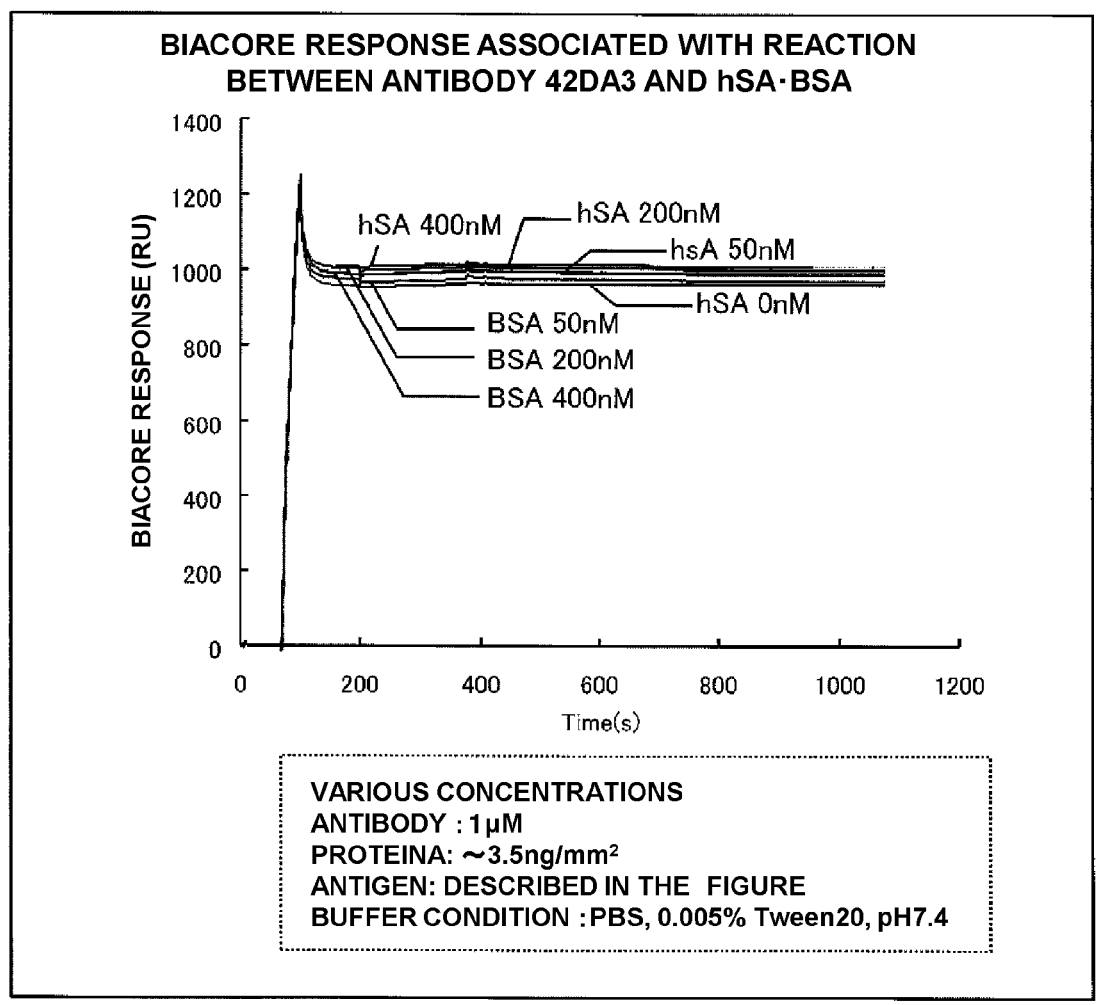
FIG. 10 is another sensor graph measured in Comparative Example 2.

FIG. 10 shows a sensorgram obtained from the measurements using antibody 42-DA3.

Figure 11:
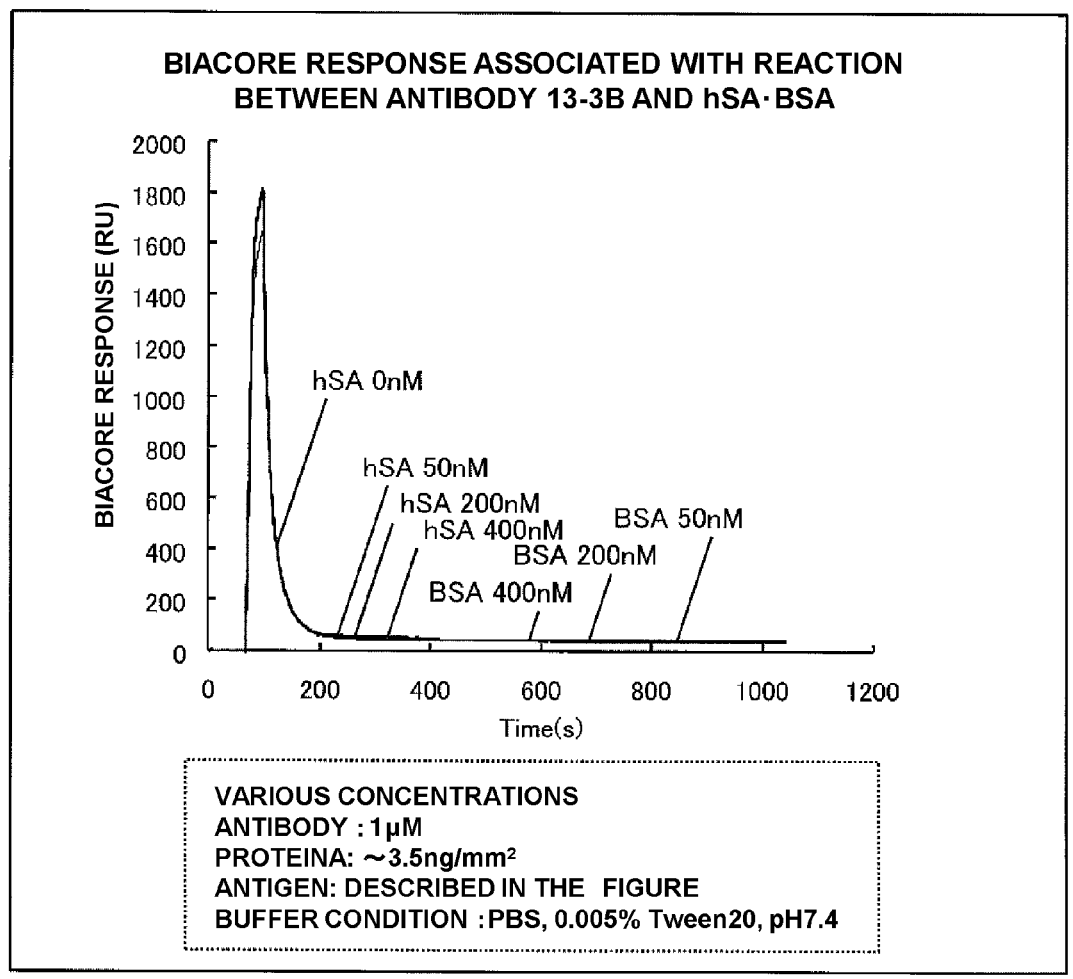
FIG. 11 is another sensor graph measured in Comparative Example 2.

FIG. 11 shows a sensorgram obtained from the measurements using antibody 13-3B.

As understood from FIGS. 9 to 11, a reduction in response was not observed when either hSA or BSA was passed through the flow cells. Therefore, only the combination of 2F13F11G11 and hSA at a pH of not lower than 6 and not higher than 8.9, preferably, a pH of not lower than 7.4 and not higher than 8.9, enables the immunoglobulin G antibody to be released from the protein A.

EXAMPLE 2

The following describes a measurement example in which the immunoassay method of the present invention is executed by a SPR device with conditions suitable for the immunoassay method.

A measuring system similar to Example 1 was used in Example 2. Thus, the following descriptions are centered on the differences in the used measuring system.

BIACORE 3000 system (manufactured by Biacore AB; hereinafter, referred to as Biacore) was used as a measuring device. Furthermore, the analyte, the antibody, and the binder used here were identical to those in Example 1. As the measuring chip, CM 5 (manufactured by Biacore AB; hereinafter, referred to as a sensor chip) was used. Protein A, which was the binder, was immobilized on the above described sensor chip through amino coupling. The amount of immobilization of protein A was around 6 $ng/mm^2$. Furthermore, in order to measure a blank value, a sensorgram was obtained at a condition in which protein A does not become immobilized onto the flow cell.

Next, PBS buffer solutions (pH 7.4) containing 0.005% TWEEN 20 and having various NaCl concentrations were prepared. The concentrations of NaCl were 0 g/l, 4 g/l, 8 g/l, 16 g/l, or 32 g/l. 2F13F11G11 was dissolved in each of the obtained PBS buffer solutions. This series of 2F13F11G11 solutions were passed through all the four flow cells at a condition of a flow rate of 20 µl/min and a flow volume of 40 µl to bind to protein A immobilized on the sensor chip. Here, the concentration of the 2F13F11G11 that have been bound was 1 µM.

After 2F13F11G11 was passed through the flow cells, the buffer solution alone was passed through the flow cells in order to remove any influences of substances other than the 2F13F11G11 bound to protein A. Next, a buffer solution having hSA dissolved therein, which was the analyte, was passed through the flow cells to allow reaction with 2F13F11G11. Here, the flow rate was 20 µl/min, and the flow volume was 40 µl. The concentration was 1 µM. These operations were performed on each of the five types of buffer solutions described above.

Figure 5:
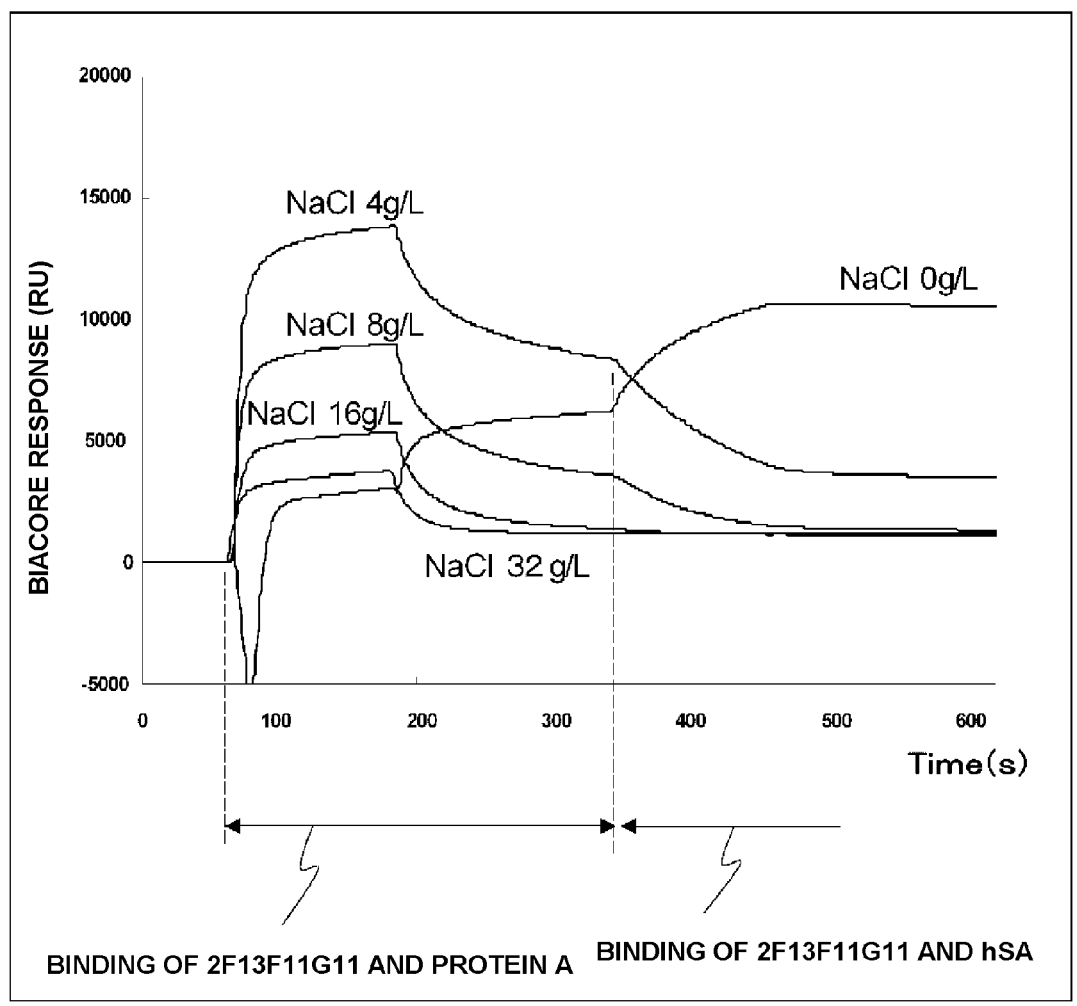
FIG. 5 is a sensor graph measured in Example 2.

FIG. 5 shows a sensorgram obtained from the measurements. The sensorgram shows results obtained by subtracting the blank value, which is obtained without the immobilized protein A, from each of the measured values. A large change in the amount of binding between protein A and 2F13F11G11 was observed in the five types of buffer solutions depending on the NaCl concentration. When the NaCl concentration was 0 g/l, an increase in the response was observed even when the buffer solution was passed through the flow cells; therefore, it is conceivable that this is a condition in which nonspecific reactions are likely to occur. The condition was perceived as being not suitable for measuring the analyte. The following observation results were obtained from the buffer solutions containing NaCl at 4 g/l or higher. The buffer solutions having a lower salt concentration tended to exhibit a larger binding amount of 2F13F11G11. Furthermore, the buffer solutions having a lower salt concentration exhibited a larger amount of the complex of hSA and 2F13F11G11 released from protein A when hSA was passed through the flow cells.

Figure 6:
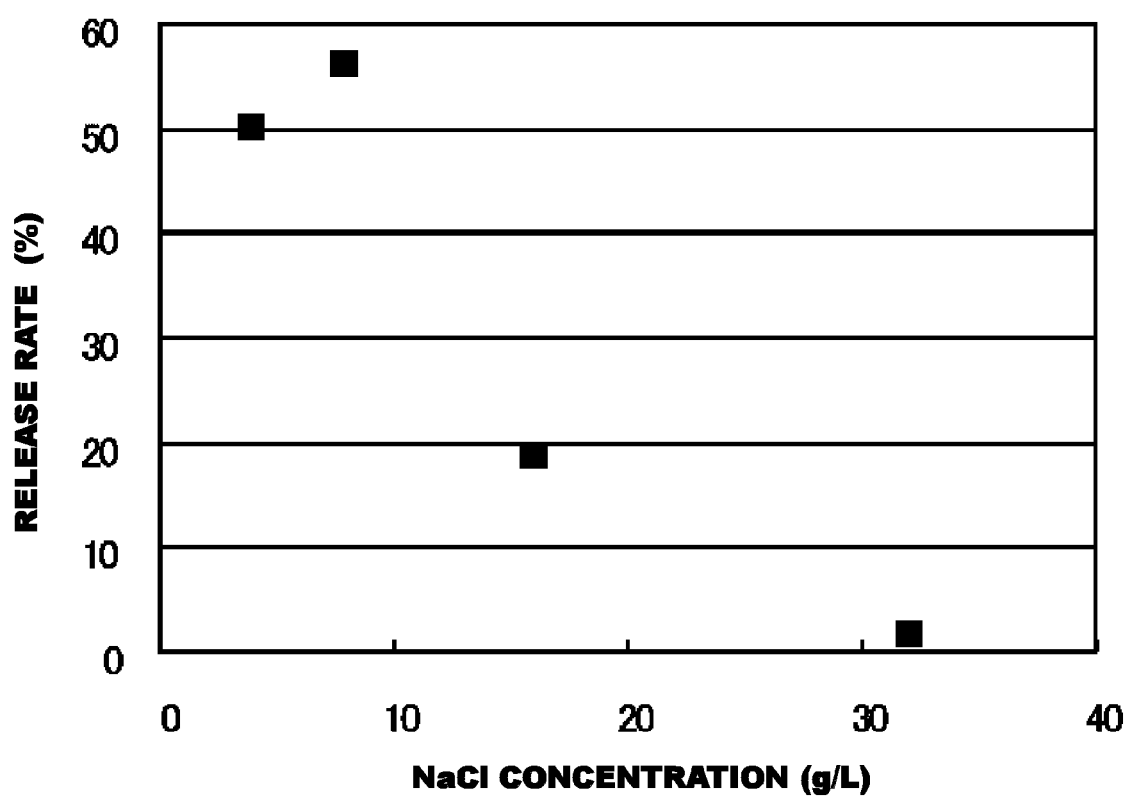
FIG. 6 is a graph indicating the relationship of release rate to salt concentration in Example 2.

FIG. 6 shows a relationship between the NaCl concentration and the amount of releasing. A release rate represented as % in the graph in FIG. 6 indicates a ratio of reduction in the BIACORE response when hSA was added, wherein a BIACORE response obtained after passing 2F13F11G11 through the flow cells but immediately before adding hSA was defined as 100%. However, since the releasing was not observed when the NaCl concentration was 0 g/l, the resulting data is not shown. As understood from FIG. 6, the release rate was high when the buffer solution containing 4 g/l or 8 g/l of NaCl was used.

These results indicate that, by using a buffer solution containing NaCl at 4 g/l to 8 g/l, a higher sensitivity can be achieved for the immunoassay method using an antibody released from protein A.

Shown next is a result of investigating the pH and the type of the buffer solution in order to obtain a suitable condition for the immunoassay method of the present invention. The measuring system used here was similar to that used for the measurement with the SPR device described above.

The following buffer solutions were prepared: a PBS buffer solution (pH 7.4) containing 0.005% Tween 20 with a NaCl concentration of 8 g/l; a PBS buffer solution (pH 8.9) containing 0.005% Tween 20 with a NaCl concentration of 8 g/l; and a Gly buffer solution (pH 8.9) containing 0.005% Tween 20 with a NaCl concentration of 8 g/l. 2F13F11G11 was dissolved in each of these prepared buffer solutions.

The obtained 2F13F11G11 solutions were passed through all the four flow cells at a condition of a flow rate of 20 µl/min and a flow volume of 40 µt to bind to protein A immobilized on the sensor chip. Here, the concentration of the 2F13F11G11 dissolved in the buffer solution was 1 µM. After passing 2F13F11G11 through the flow cells, the buffer solution alone was passed through the flow cells in order to remove any influences of substances other than the 2F13F11G11 bound to protein A. Next, a buffer solution having hSA dissolved therein, which was the analyte, was passed through the flow cells to allow reaction with 2F13F11G11. Here, the flow rate was 20 µl/min, the flow volume was 40 and the concentration was 1 µM.

Figure 7:
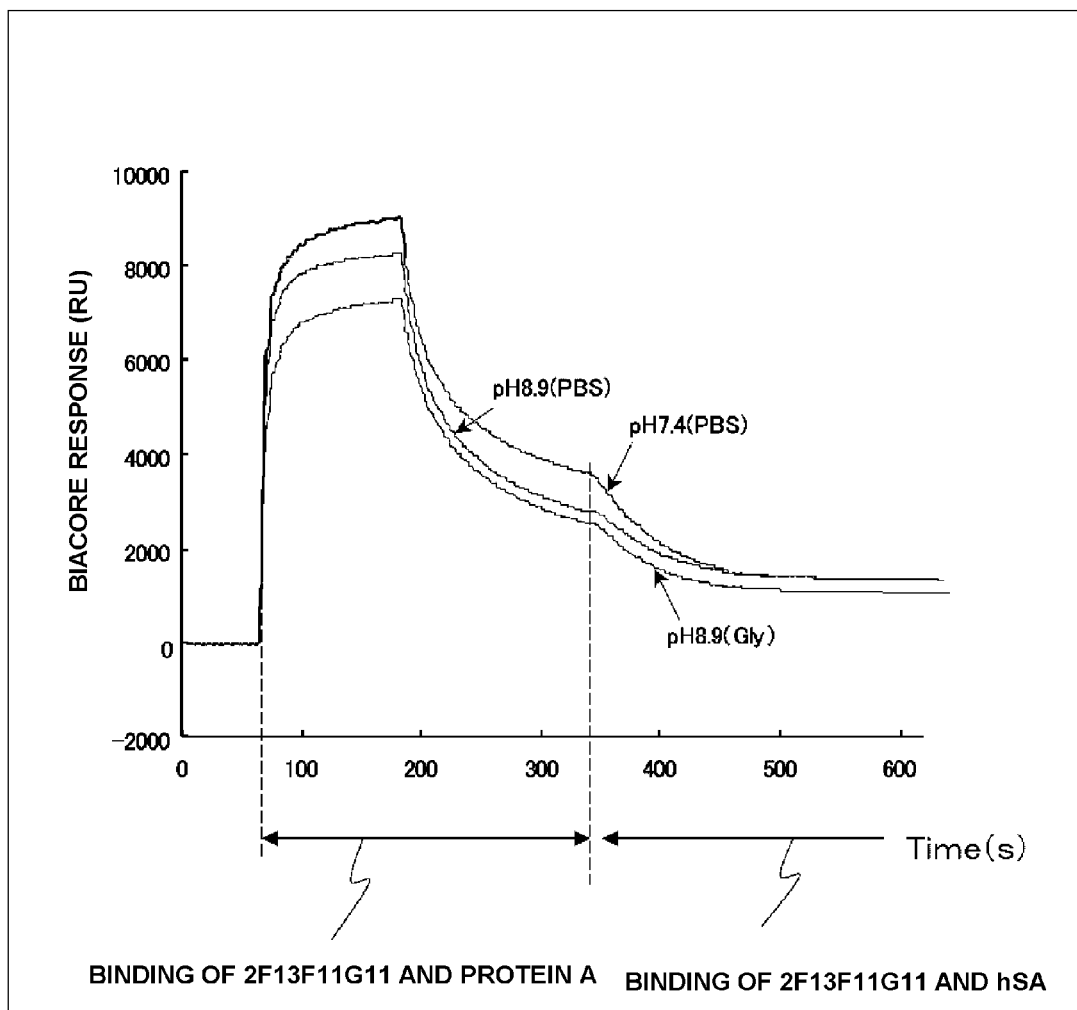
FIG. 7 is a sensor graph indicating the relationship of release rate to the type and pH of a buffer solution in Example 2.
Figure 8:
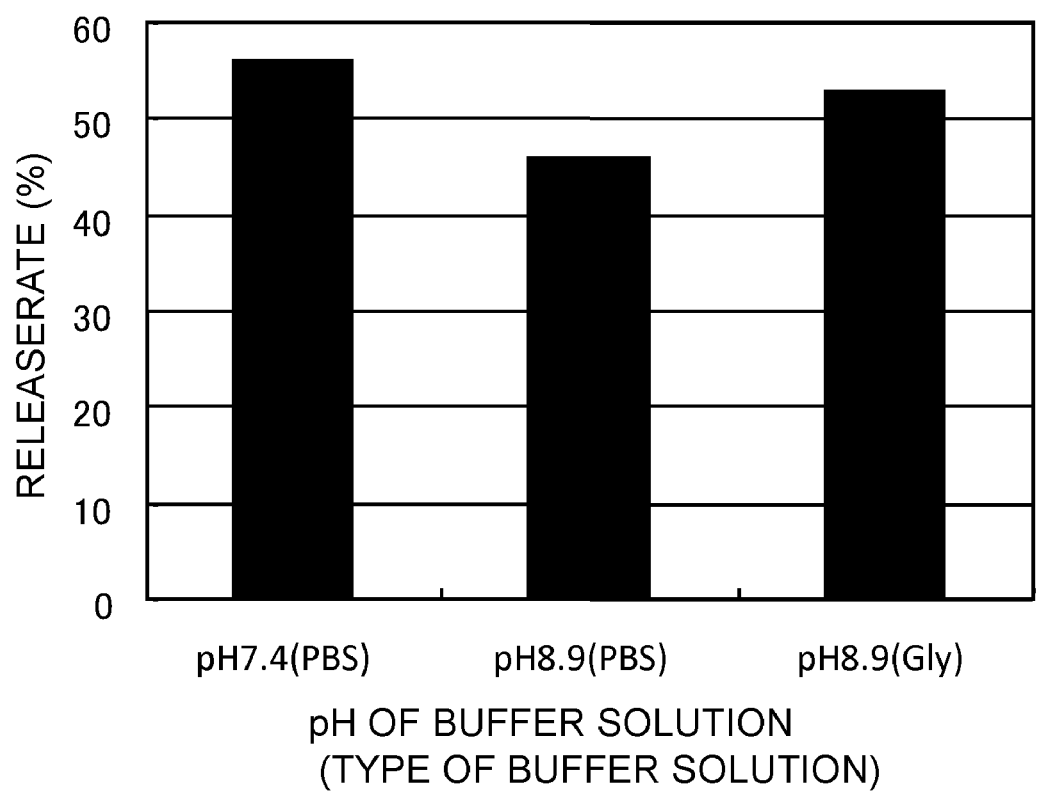
FIG. 8 is a graph showing the relationship of release rate to the type and pH of the buffer solution in Example 2.

FIG. 7 shows a sensorgram obtained from the respective buffer solutions. FIG. 8 shows release rates in association with the addition of hSA. The release rates were calculated based on the result shown in FIG. 7. Although a difference in the binding amount of 2F13F11G11 is observed in FIG. 7 depending on the pH and the type of the buffer solution, it is understood from FIG. 8 that the difference in the release rates due to the difference in the pH and the type of the buffer solution is small. Therefore, the measuring system described above is applicable at least when either a PBS buffer solution or a Gly buffer solution is used. In addition, the above described results indicate that the measuring system is applicable also in a pH range from pH 7.4 to pH 8.9.

While the invention has been described in detail, the foregoing description is in all aspects illustrative and not restrictive. It will be understood that numerous other modifications and variations can be devised without departing from the scope of the present invention. It should be understood that the scope of the present invention is definitely interpreted only on the basis of the scope of the claims. Furthermore, it should be understood that a person ordinarily skilled in the art can carry out an equivalent scope of invention based on the descriptions of the present invention and the common technological knowledge, by referring to the descriptions of the specific preferred embodiments of the present invention. It will be understood as a matter of course that throughout the present specification, unless otherwise particularly stated, a singular expression encompasses the concept of plurality as well. Therefore, it will be understood as a matter of course that, unless otherwise particularly stated, a singular article or adjective (e.g., "a", "an", "the" or the like in English) encompasses the concept of plurality as well. Furthermore, it will be understood as a matter of course that, unless otherwise particularly stated, the terms used in the present specification are used in the meaning as conventionally used in the related art. Therefore, unless defined otherwise, all the jargon and technical terms used in the present specification have the same meanings as generally understood by those skilled in the art to which the present invention is pertained. In the case of contradiction, the present specification (including the definitions) dominates.

INDUSTRIAL APPLICABILITY

The present invention achieves an immunoassay system with a single type of antibody that specifically binds to an antigen. As a result, the effort of establishing an immunoassay system can be reduced. In addition, since it is not necessary to use two types of antibodies that specifically bind to an antigen to form a sandwich-like binding unit, the present invention may be used for an antigen having a low molecular weight, such as hapten.

REFERENTIAL SIGNS LIST 11 support
101 analyte
102 antibody
103 label
104 binder
105 antibody-binder complex
106 binder binding cite
111 immunochromatographical test piece
112 PTFE base plate
113 nitrocellulose membrane
114 sample solution introduction portion
115 liquid absorptive pad
116 second antibody

What is claimed is:

1. A method for releasing, from a surface of a base plate, immunoglobulin G antibody bound to the surface via protein A, the method comprising the following steps (A) and (B):
   a step (A) of preparing the base plate having the surface to which immunoglobulin G antibody is bound via protein A by supplying a buffer solution containing sodium chloride and the immunoglobulin G antibody to the surface of the base plate where the protein A has been immobilized; wherein
   the concentration of the sodium chloride contained in the buffer solution is not less than 4 g/liter and not more than 16 g/liter, and
   a step (B) of providing a solution containing human serum albumin onto the surface so as to release the immunoglobulin G antibody from the protein A, wherein
   the immunoglobulin G antibody is an anti-human albumin monoclonal antibody 2F13F11G11 produced by a producer cell line of deposit No. FERM BP-10459,
   the solution has a pH not lower than 6 and not higher than 8.9, and
   in the step (B), a complex of the immunoglobulin G antibody and the human serum albumin is formed through antigen-antibody reaction.

2. The method according to claim 1, wherein the immunoglobulin G antibody is released from the surface when the complex is formed.

3. The method according to claim 1, wherein the solution contains the immunoglobulin G antibody which has been released from the surface after the step (B).

4. The method according to claim 1, wherein the solution contains the complex after the step (B).

5. The method according to claim 1, wherein the pH is not lower than 7.4 and not higher than 8.9.

6. The method according to claim 1, wherein the solution is a buffer solution.

7. The method according to claim 6, wherein the pH is not lower than 7.4 and not higher than 8.9.

8. A method for quantifying human serum albumin contained in a solution, the method comprising the following steps (A), (B), and (C):
   a step (A) of preparing a base plate having a surface to which immunoglobulin G antibody is bound via protein A by supplying a buffer solution containing sodium chloride and the immunoglobulin G antibody to the surface of the base plate where the protein A has been immobilized;
   the immunoglobulin G antibody is modified with a label,
   the immunoglobulin G antibody is an anti-human albumin monoclonal antibody 2F13F11G11 produced by a producer cell line of deposit No. FERM BP-10459; and
   the concentration of the sodium chloride contained in the buffer solution is not less than 4 g/liter and not more than 16 g/liter, and
   a step (B) of providing a solution containing human serum albumin onto the surface so as to release the immunoglobulin G antibody from the protein A and to mix the immunoglobulin G antibody into the solution, wherein the solution has a pH not lower than 6 and not higher than 8.9; wherein
   a complex of the immunoglobulin G antibody and the human serum albumin is formed through antigen-antibody reaction, and
   a step (C) of quantifying the label with which the immunoglobulin G antibody mixed into the solution is modified, to quantify the human serum albumin contained in the solution.

9. The method according to claim 8, wherein the immunoglobulin G antibody is released from the surface when the complex is formed.

10. The method according to claim 8, wherein the solution contains the immunoglobulin G antibody which has been released from the surface after the step (B).

11. The method according to claim 8, wherein the solution contains the complex after the step (B).

12. The method according to claim 8, wherein the pH is not lower than 7.4 and not higher than 8.9.

13. The method according to claim 8, wherein the solution is a buffer solution.

14. The method according to claim 13, wherein the pH is not lower than 7.4 and not higher than 8.9.

15. A method for determining whether a solution contains human serum albumin, the method comprising the following steps (A), (B), (C), and (D):
   a step (A) of preparing a base plate having a surface to which immunoglobulin G antibody is bound via protein A by supplying a buffer solution containing sodium chloride and the immunoglobulin G antibody to the surface of the base plate where the protein A has been immobilized, wherein
   the immunoglobulin G antibody is modified with a label,
   the immunoglobulin G antibody is an anti-human albumin monoclonal antibody 2F13F11G11 produced by a producer cell line of deposit No. FERM BP-10459,and
   the concentration of the sodium chloride contained in the buffer solution is not less than4 g/liter and not more than 16 g/liter,
   a step (B) of providing a solution predicted to contain human serum albumin onto the surface so as to release the immunoglobulin G antibody from the protein A and to mix the immunoglobulin G antibody into the solution, wherein the solution has a pH not lower than 6 and not higher than 8.9; and
   a complex of the immunoglobulin G antibody and the human serum albumin is formed through antigen-antibody reaction,
   a step (C) of detecting the label with which the immunoglobulin G antibody mixed into the solution is modified; and
   a step (D) of, if the label is detected in the step (C), determining that the solution contains the human serum albumin.

16. The method according to claim 15, wherein the immunoglobulin G antibody is released from the surface when the complex is formed.

17. The method according to claim 15, wherein the solution contains the immunoglobulin G antibody which has been released from the surface after the step (B).

18. The method according to claim 15, wherein the solution contains the complex after the step (B).

19. The method according to claim 15, wherein the pH is not lower than 7.4 and not higher than 8.9.

20. The method according to claim 15, wherein the solution is a buffer solution.

21. The method according to claim 20, wherein the pH is not lower than 7.4 and not higher than 8.9.

* * * * *